US00PP09241P

United States Patent [19]

Green

[11] Patent Number: Plant 9,241

[45] Date of Patent: Aug. 15, 1995

[54] 'GREEN DIAMOND' NAVEL

[76] Inventor: Scott E. Green, P.O. Box 449, Dundee, Fla. 33838

[21] Appl. No.: 259,637

[22] Filed: Jun. 14, 1994

[51] Int. Cl.[6] ..... A01H 5/00

[52] U.S. Cl. ..... Plt./45

[58] Field of Search ..... Plt. 45

*Primary Examiner*—James R. Feyrer

*Attorney, Agent, or Firm*—Jones & Askew

[57] ABSTRACT

A new and distinct variety of Valencia navel orange tree which is characterized by seedless fruit with a navel structure and has a very late maturity.

2 Drawing Sheets

FIELD OF THE INVENTION

The present invention relates to a new and distinct variety of orange tree known as 'Green Diamond' Navel. More particularly, the present invention relates to an orange tree which produces seedless navel oranges which are characterized by a navel on the apex end and the late maturity.

BACKGROUND OF THE INVENTION

Florida produces a large percentage of the world's supply of grapefruit and about a quarter of the world's supply of oranges. Of the oranges that are produced in Florida, the Valencia orange is the leading commercial fruit. Most of the Valencia oranges produced in Florida are processed into frozen orange juice concentrate. Unlike Valencia oranges, navel oranges comprise only about five percent of the total number of oranges produced in Florida and are grown primarily for the fresh fruit market.

The most distinctive anatomical characteristic of navel orange fruit is the presence of the navel in the apex of the fruit. The navel results from a small, rudimentary secondary fruit embedded in the primary fruit. The navel orange tree is the only kind of orange tree which consistently produces fruit with navels.

In Florida, navel orange fruit matures in November and December. The parent Green Diamond Navel tree is more than fifty years old. The trunk of the tree is 45.5 inches in circumference and the height of the tree is approximately 19.5 feet. The canopy of the tree is approximately 19 feet and 9 inches. The tree is a constant bearer and does not require cross pollination. The blooms of the tree produce pollen.

The trees of the twenty-five acre block of trees where the parent Green Diamond Navel tree is planted are Valencia orange trees and Hamlin orange trees. Approximately fifteen acres are planted in Valencia orange trees and ten acres are planted in Hamlin orange trees. The Green Diamond Navel orange tree is within the Valencia section of the block. Eight-five percent of the planted trees were planted at the same time, approximately fifty years ago. The inventor is responsible for any reset trees in the block. The reset trees which are present are obviously smaller and stand out among the orignial old trees.

The parent Green Diamond Navel tree was mature when discovered and had been bearing fruit for many years. The parent tree is grafted budwood and the entire tree exhibits the novel characteristics described. Because the surrounding trees planted in the same block of the grove are Valencia orange trees and all of the trees were planted at the same time, the budwood source of the parent tree was probably Valencia. There are no Washington navels grown in the grove currently, nor were any present years ago when the parent tree was planted. Because the fruit of the instant tree is distinctively different from a Washington navel, for example, in taste and size, the instant tree is not a sport of a Washington navel. The parent tree is grafted onto rough lemon stock, as determined by citrus experts, including U.S.D.A. citrus research personnel. The parent tree is located in a cultivated grove in Polk County, Fla., approximately three miles east of Dundee, Fla.

The Green Diamond Navel clones produced from budwood of the parent tree have been grafted onto Milan, Swingle Citrumelo and Smooth Flat Seville rootstocks. The clones exhibit a very vigorous growth rate that is markedly different from any other species in the inventor's nursery under the same growing conditions. The clones were asexually reproduced by the inventor in early 1993 in the inventor's citrus nursery near Dundee, Fla. The clones have the same morphological characteristics of the parent tree, including the distinctive leaf characteristics and the navel fruit.

The Green Diamond Navel has characteristics which are distinctive from other types of navels, such as the Lang navel, the Washington navel and the DPI (Department of Plant Industry) navel. The fruit of the Green Diamond Navel differs from all other navels in that the fruit of the Green Diamond Navel is ripe in the warm summer months of May, June and July, whereas other navels ripen in the Fall and winter months of November and December. The size of the fruit of the Green Diamond Navel is distinctly different from the large-sized Washington navel. Washington navels have large fruit with average diameters of 3.5 to 4 inches, whereas DPI navel fruit averages from 3.25 to 3.5 inches in diameter, and the Green Diamond Navel has fruit with average diameter of 3.25 to 3.38 inches. Washington navel fruit is not only larger in size, but also has a thicker rind, a different color and a different taste from the Green Diamond Navel fruit.

The Green Diamond Navel has characteristics which are also distinctive from Valencia orange trees. The most distinctive characteristic is the navel structure which is always present in the fruit of the Green Diamond Navel. The navel is small, and approximately seventy-five percent of the navels are closed and even. The smell of the Green Diamond Navel fruit is very distinctive from that of a Valencia fruit. Unlike Valencia fruit, the Green Diamond Navel fruit is virtually seedless. In twenty-four random samples only 2 seeds were found.

SUMMARY OF THE INVENTION

The 'Green Diamond Navel' orange tree is characterized by producing a late maturing, seedless fruit with a navel on the apex of the fruit, has the taste of a navel orange and a rind which is similar to that of a Valencia orange.

BRIEF DESCRIPTION OF THE DRAWINGS

The accompanying figures illustrate typical specimens of the fruit and foliage of the present invention's new variety of navel orange tree as grown in Florida.

Figure 1:
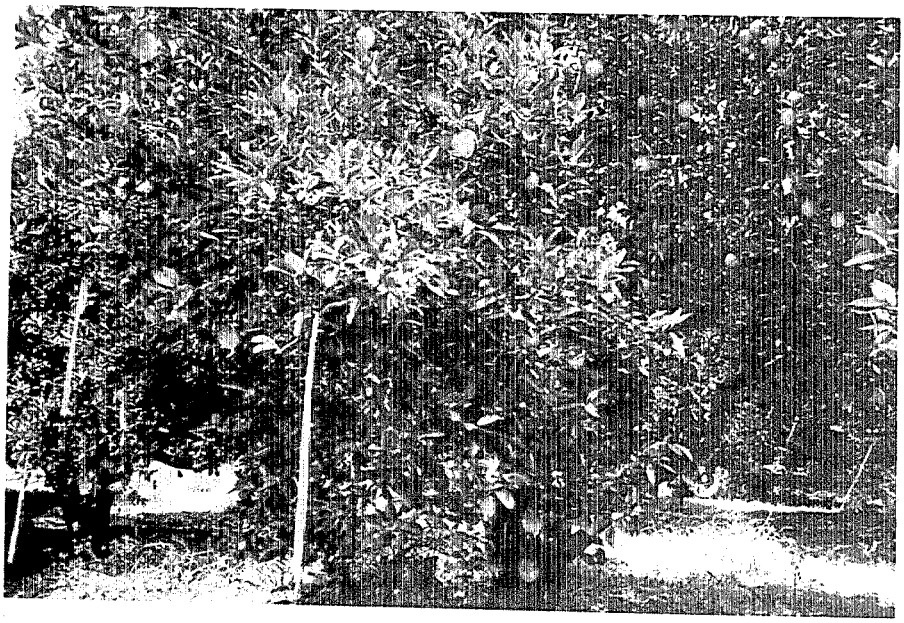
FIG. 1 shows the foliage and shape of the new and distinct Valencia navel orange tree.
Figure 2:
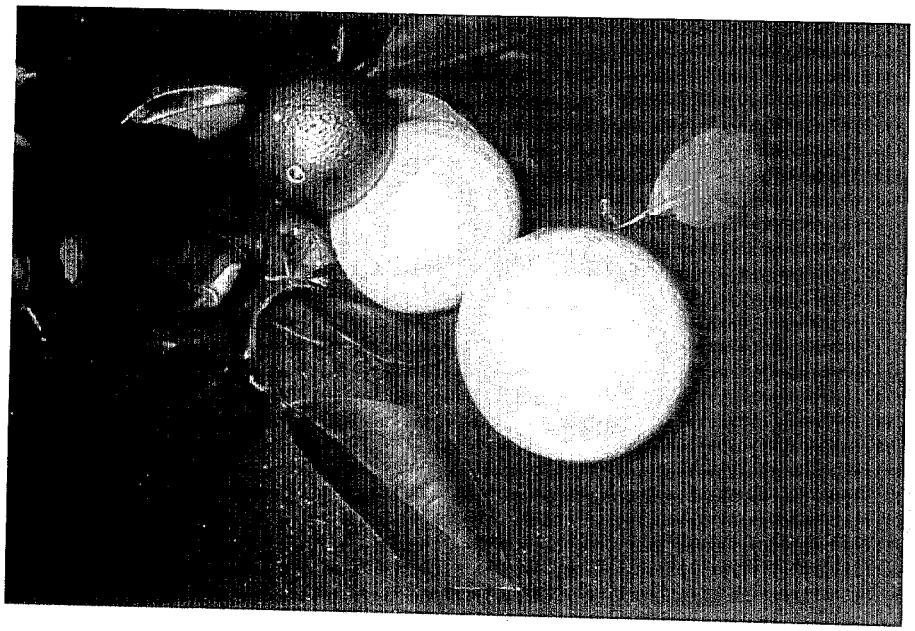
FIG. 2 shows the fruit and leaves the new and distinct Valencia navel orange tree.
Figure 3:
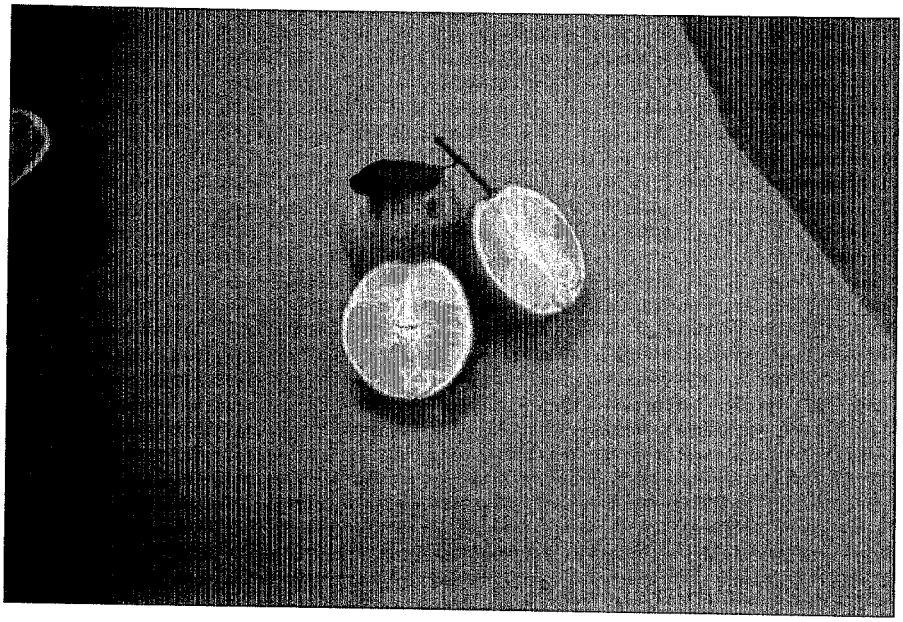
FIG. 3 shows the fruit of the new and distinct Valencia navel orange tree which is cut so that the embedded navel is visible.
Figure 4:
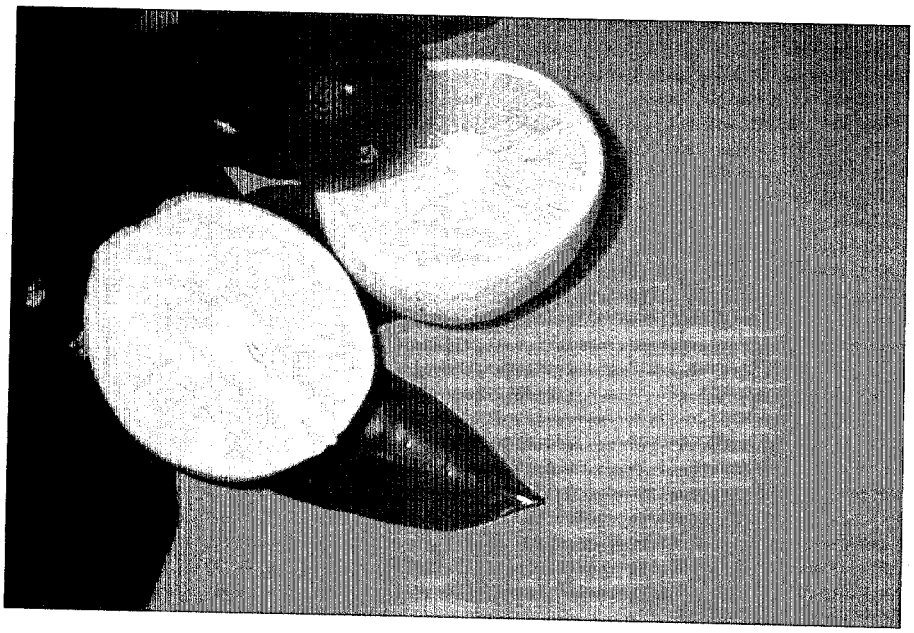
FIG. 4 shows a closer view of the fruit with the fruit cut to show the number of segments in a typical fruit and another cut showing the embedded navel in a typical fruit.

The coloration of the bark, foliage and fruit of the plant of this discovery is has not been viewed to fall outside the normal range of color expressions for either the "Valencia" variety or navel orange market class, and would not particularly characterize the tree described herein.

DETAILED DESCRIPTION

The following is a detailed description of the new and distinct variety of navel orange tree of the present invention.

The original Green Diamond Navel orange tree is in a cultivated grove 3 miles east of Dundee, Fla., where it has been growing for more than fifty years. The clones are grown and observed in the Inventor's nursery in Dundee, Fla. The parent tree is Valencia budwood which was grafted onto rough lemon rootstock. The budwood scions have been grafted on Milam, Swingle Citrumelo and Smooth Flat Sevill rootstocks.

The mature height of the Green Diamond Navel orange tree is 19.5 feet, with a trunk circumference of 45.5 inches and a canopy of 19.75 feet. The shape is similar to that of the Valencia trees growing around the tree and the tree has a moderate number of thorns. The surrounding Valencias have no thorns. There are no navel orange trees in the block of trees surrounding the Green Diamond Navel, nor any of the area surrounding the tree.

The budded trees show an extraordinary rate of growth and vigor. They are noticeably more vigorous than other trees in the nursery, including budded Valencias and other types of navels.

Wood

The mature wood of the Green Diamond Navel has relatively smooth bark of greenish brown color, similar to that of Valencia or navel orange trees. The new bark has a much lighter green color, and is similar to new bark of Valencia and navel orange trees. The limbs of the Green Diamond Navel have a generally rounded shape and irregular array.

Foliage

The single leaf of the Green Diamond Navel is more pointed at the leaf tip and has a more narrowed shape throughout the leaf than either Valencia or navel leaves. The Valencia leaf has a more rounded appearance.

The Green Diamond Navel leaf has an average size of 87 mm length, and 44 mm width, at the widest section. When comparing leaves of approximately the same length, the width of the Green Diamond Navel is less than the Valencia leaf width and also less than the width of Washington navel, Lang navel or DPI navel leaves.

The veins of the Green Diamond Navel branch from the midrib and curve along the margins. A vein branches from the midrib and curves prior to the margin and appears to interconnedt with the next lower vein. The midrib of the Green Diamond Navel leaf is less prominent than that of either Valencia or navel leaves.

The margin of the Green Diamond Navel leaf is smooth to slightly serrated.

The upper surface of the leaf is smooth and has a medium dark green glossy appearance. The lower surface of the leaf has prominent veins, as described above, and has a lighter, yellowish green color. Leaves from various navel trees, such as Washington, Lang and DPI navel trees, have a similar color but the veins are not as prominent. The lower surface of Valencia leaves are a similar color.

The stem wing of the Green Diamond Navel is distinctly different from that of Valencia or navel leaves. The Green Diamond Navel stem wing has a long narrow winged shape, whereas Valencia stem wings are wider and shorter in shape. Navel stem wings from Washington navel, Lang navel and DPI navel are noticeably longer than the stem wing from the Green Diamond Navel. The Green Diamond Navel stem wing is approximately 3.5 to 4.5 mm at the widest point, whereas Valencia stem wings are approximately 5.5 to 7 mm at the widest point. The navel stem wing varies depending on the type of navel: Washington navel have 7 to 9 mm width, Lang navel have 6 to 9 mm width, and DPI navel have 5 to 7 mm width.

Bloom Date

The Green Diamond Navel blooms in approximately February or March, depending on the weather conditions in Florida. This bloom date is approximately the same time as the Valencia orange trees grown in the same section of Florida. Blossom color or character has not been noted to differ from the surrounding trees. The blossoms have pollen present.

Fruit

All of the fruit from the Green Diamond Navel orange tree has the characteristic navel. The Green Diamond Navel fruit has a very tight, small navel on the apex end. The navel is smaller and tighter than the Washington, Lang or DPI navel oranges. The Green Diamond navel appearance ranges from a small button to a raised lump. An inside cross-section of the orange fruit shows the navel is present as a protruding upward growth of the rudimentary secondary fruit to the center of the primary fruit. Seventy-five percent of the navels are closed.

The shape of the fruit of the Green Diamond Navel is more than a Valencia orange except for the presence of the navel. The shape of the fruit is oblong to oval with an average length of 80 to 90 mm and an average width of 64 to 70 mm. Valencia orange fruit is generally classified as oval whereas most navel fruit is oblong.

The rind of the fruit of the Green Diamond Navel has a texture which is medium coarse to slightly dimpled. The peel of Valencia fruit is smoother than the Green Diamond Navel whereas navel fruit, from DPI navel or Washington navel, has a coarse texture and are slightly dimpled.

The thickness of the rind of the Green Diamond Navel is similar to that of Valencia orange fruit, with an approximate thickness of 3 mm. Washington navel fruit has a thicker rind, of approximately 5 mm, and the Lang or DPI navel fruit has an approximately 4 mm thick rind.

The Green Diamond Navel fruit is easy to peel, much like a navel orange, and has a navel orange smell.

The number of oil cells is medium, with approximately 30 per cubic centimeter. The color of the fruit is yellowish orange. Regreening can occur in July and August, and is similar to the regreening seen in Valencia oranges. There is no late season puffing seen in the Green Diamond Navel fruit.

The fruit of the Green Diamond Navel is seedless. In 24 random samples of the fruit, only 2 seeds were found. There are approximately 13 to 14 segments per fruit, whereas Valencia oranges have 10–11 segments and Washington navels have 10 segments. There is a thin layer of membranes between the segments of the Green Diamond Navel fruit. There is a large central columella in the Green Diamond Navel that is larger than that seen in Valencia or Washington navel oranges.

There is noticeably abundant amount of juice produced by the Green Diamond Navel fruit. The juice color is deep orange, U.S.D.A. color score 37, as determined with a Hunter Lab Citrus Colorimiter. This color is darker than navel orange juice color. Valencia juice can be this color or darker.

No off-flavors develop in the Green Diamond Navel fruit as the season of maturing progresses. The Green Diamond Navel fruit has a low level of liminon present in the juice.

A test of the juice of the Green Diamond Navel showed that the acid content was high compared to Valencia fruit. In June, a test showed that the Green Diamond Navel fruit has 0.95 to 1.20 acid, Valencia oranges had acid below 0.65. Valencia orange juice may average 0.68 to 0.74 at peak maturity.

A Jun. 6, 1994, U.S.D.A. juice test showed at 56.623 percent juice content. The test also showed that acid remained high with favored Brix, results were: Acid 0.98; Brix 14.26; Ratio 14.55.

The average pounds solid of the Green Diamond Navel is higher than that of Valencia or navel oranges. The average pound solids of the Green Diamond Navel is 8.07 whereas the Valencia is 7.2 and navels are 5.5

Average Brix determinations also distinguish the Green Diamond Navel. The Brix for the Green Diamond Navel is higher than either Valencia or navel fruit. Average Brix for the Green Diamond Navel is 14.26, whereas the average Brix for Valencia is 9–10, and for other navels is 9.65.

The flavor of the Green Diamond Navel juice is mild, sweet to slightly tart. A grower panel rated to the taste as that of a navel orange.

The fruit of the Green Diamond Navel natures in late May to July, with peak maturity from approximately late May to early June.

The fruit of the Green Diamond Navel can remain on the tree through late July to mid-August. Fruit drop is minimal.

USDA Test Jun. 6, 1994

Thirty-four pieces of Green Diamond Navel fruit were tested on Jun. 6, 1994. The average results were 56.623 percent juice, the acid content was 98%, Total Brix was 14.26, the ratio was 14.55. Pound Solids per box showed 8.0744, with 7.267 pound solids per load.

Use

The fruit of the Green Diamond Navel would be sold in the fresh fruit market. A specific navel juice market could be developed based on the high pound solid characteristic of the fruit.

CULTIVAR NAME

"Green Diamond Navel"

Although this new variety of late maturing navel orange tree and its fruit exhibit the described characteristics noted above as a result of the growing conditions of Polk County, Fla., it is understood that variations of the usual magnitude and characteristics incident to changes in growing conditions, fertilization, pruning, pest control and other horticultural practices and climatological conditions are to be expected.

What is claimed is:

1. A new and distinct variety of navel orange tree substantially as shown and described, characterized particularly as to novelty by having a distinctive leaf stem wing, and by producing seedless fruit with a navel which matures in May, June or July.

* * * * *